United States Patent [19]

Goel

[11] Patent Number: 4,464,303

[45] Date of Patent: Aug. 7, 1984

[54] MANUFACTURE OF HIGHER ARYL ESTERS CROSS-REFERENCE TO RELATED APPLICATIONS

[75] Inventor: Anil B. Goel, Worthington, Ohio

[73] Assignee: Ashland Oil, Inc., Ashland, Ky.

[21] Appl. No.: 416,809

[22] Filed: Sep. 13, 1982

[51] Int. Cl.$^3$ .................. C11C 3/02; C09F 5/08
[52] U.S. Cl. ..................... 260/410; 260/410.5; 260/406; 560/131
[58] Field of Search .............. 260/410 R, 406; 560/131; 260/410.5

[56] References Cited

U.S. PATENT DOCUMENTS

| | | | |
|---|---|---|---|
| 3,493,605 | 2/1970 | Selwitz | 260/410.5 |
| 3,646,111 | 2/1972 | Hörnig et al. | 560/131 |
| 3,651,127 | 3/1972 | Hörnig et al. | 560/131 |
| 3,772,383 | 11/1973 | Kominami et al. | 560/131 |
| 4,229,587 | 10/1980 | Murib | 560/131 |

*Primary Examiner*—Mrs. Y. Harris-Smith
*Attorney, Agent, or Firm*—John F. Jones

[57] ABSTRACT

An improved process for the manufacture of higher aromatic hydrocarbon esters, such as naphthyl esters, by liquid phase reaction of the higher aromatic hydrocarbon compound with molecular oxygen in the presence of a higher carboxylic acid over a catalyst composed essentially of a compound of palladium and an antimony compound wherein the aromatic compound is dissolved in an inert solvent and is added continuously to the reaction zone and water formed in the reaction is rapidly and continuously removed from the reaction zone.

9 Claims, No Drawings

MANUFACTURE OF HIGHER ARYL ESTERS CROSS-REFERENCE TO RELATED APPLICATIONS

CROSS-REFERENCE TO RELATED APPLICATIONS

This invention is an improvement over the process more fully described and claimed in the copending U.S. patent application Ser. No. 348,561, filed Feb. 12, 1982, by Anil B. Goel and Robert A. Grimm. Improved catalysts of the type described herein are also described in the copending U.S. patent application of Anil B. Goel and Peter E. Throckmorton, Ser. No. 441,360, filed Oct. 15, 1982.

BACKGROUND OF THE INVENTION

1. Field of the Invention

The present invention provides an improved process for making higher aryl esters from higher aromatic compounds such as naphthalene, anthracene, biphenyl, phenanthrene, terphenyls, and the like, which comprises reacting a solution of the higher aromatic compound, such as a solution of naphthalene in hexane, with molecular oxygen and a higher carboxylic acid in the liquid phase in the presence of a catalyst which is composed of palladium or a compound of palladium, a compound of antimony and optionally a compound of a metal selected from the group consisting of chromium, cobalt, nickel, manganese, iron and tin.

2. Description of the Prior Art

The manufacture of phenol by the direct oxidation of benzene with oxygen is known. There are, for instance, thermal processes which are performed at very high temperatures in which the phenol formed is susceptible to further oxidation so that considerable loss of yield occurs as is disclosed in U.S. Pat. No. 2,223,383. In the presence of catalysts, the oxidation can be carried out at somewhat lower temperatures as in U.S. Pat. No. 3,133,122 but the reactions have been plagued by low conversions and excessive production of unwanted by-products as is disclosed in U.S. Pat. No. 2,392,875.

It already has been proposed to make phenyl acetate and biphenyl from benzene and acetic acid in the liquid phase in the presence of palladium acetate and without added molecular oxygen by a stoichiometric reaction in *CHEM. AND IND.*, Mar. 12, 1966, page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently the preparation of phenyl esters and phenols by the reaction of benzene, molecular oxygen and a lower aliphatic carboxylic acid in the presence of a catalysts composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc. are disadvantageous for an industrial process. U.S. Pat. No. 3,772,383 describes a liquid phase reaction using a very complex catalyst system which includes the use of nitric acid and a lower aliphatic carboxylic acid such as acetic, propionic, n-butyric, isobutyric, or caproic acid. Generally speaking these prior art processes deal for the most part with vapor phase oxidation reactions, or liquid phase reactions in which all the reactants (except oxygen in some instances) are initially included in the reaction mixture, they use lower aliphatic carboxylic acids such as acetic acid and propionic acid, and they often require an alkali or alkaline earth metal carboxylate as part of the catalyst. Moreover, in general the prior art catalytic processes have produced very low conversions, usually less than 10%, with poor selectivity to the desired phenyl ester, and phenol is often a primary product. The use of the lower saturated carboxylic acids, primarily acetic acid, in the prior art processes produce a highly corrosive system which can cause reaction equipment problems and excessive recycle costs as well as the poor conversions and selectivities mentioned above. None of the prior art processes disclose the continuous addition of the aromatic hydrocarbon and the continuous removal of water from the reaction mixture as it forms nor do they disclose or suggest the use of a solvent for higher aromatic compounds in the oxidation process.

SUMMARY OF THE INVENTION

I have discovered an improved oxidation process for the transformation of higher aromatic hydrocarbons containing 10 or more carbon atoms and two or more aromatic rings such as naphthalene, anthracene, biphenyl, phenanthrene, terphenyls, and the like, molecular oxygen and a higher carboxylic acid to the corresponding aromatic carboxylate in high conversions and selectivities to the desired product by including a solvent for the aromatic hydrocarbon in the process. Our discovery is based upon the use of mono or poly-carboxylic acids having 5 or more carbon atoms as well as the use of a certain type of palladium-antimony catalyst in conjunction with the use of the solvent for the higher aromatic hydrocarbon in my process.

I have also discovered that our liquid phase reaction produces high conversions and substantially quantitative yields of higher aryl esters when the higher aromatic hydrocarbon is either reacted with carboxylic acid in the presence of an inert solvent or is continuously added in solution in an inert solvent to the reaction mixture during the entire course of the reaction and the solvent is preferably continuously removed from the reaction mixture during the entire course of the reaction. The solvent can be one which has the ability to remove water by entrainment so that water formed as the higher aromatic hydrocarbon is converted to ester is continuously removed from the reaction mixture in the process. If water, which is a by-product of the oxidation reaction, is allowed to remain in the reaction mixture, it can cause hydrolysis of the aryl ester to produce aromatic hydroxy compounds which in turn can cause fouling and inactivation of the catalyst.

The catalysts useful in my process are preferably composed of palladium metal or compounds of palladium and usually a palladium carboxylate for convenience in conjunction with an antimony compound and usually an antimony carboxylate and optional specific metal carboxylates also may be present. The use of significant amounts of other materials such as those disclosed as being catalyst promoters in the prior art in addition to the essential palladium and antimony and specified optional metal components of my catalyst is usually detrimental to our process. The catalysts of this invention may be used alone or may be supported on a carrier or carriers. Suitable carriers include silica, alumina, carbon, quartz, pumice, diatomaceous earth, and the like and others which are known in the art.

The carboxylic acids useful in my invention include mono and poly-carboxylic acids having 5 or more carbon atoms which correspond to the formula $R(COOH)_n$ wherein n is an integer of 1 or more and R is a hydrocarbon group having at least 5−n carbon atoms. Some carboxylic acid anhydride can be included with the carboxylic acid in the reaction if desired.

For the higher aromatic hydrocarbons organic solvents which also may be useful for the entrainment and removal of water from the reaction mixture include linear hydrocarbons having the formula $C_nH_{2n+2}$ wherein n is from 4 to 14 such as heptane, pentane, hexane, octanes and the like, cyclic hydrocarbons having the formula $C_nH_{2n}$ wherein n is from 4 to 14, and linear and cyclic aliphatic ethers.

The process of this invention produces in the case of naphthalene reactant conversions of the carboxylic acid in the order of 10% or greater with selectivities to the naphthyl ester on the order of 100%. Thus, our process produces desired product in such significant quantities that it is directly competitive with the best of the present day commercial processes for the manufacture of alpha and beta naphthyl esters and naphthols themselves. The naphthyl esters which are produced by the process of this invention can be readily converted to the corresponding naphthols and the corresponding carboxylic acid by known methods for hydrolysis or pyrolysis. The naphthols are easily recovered by known means and the carboxylic acid, ketene or acid anhydride is readily recycled for further use in the oxidation reaction of this invention.

DESCRIPTION OF THE PREFERRED EMBODIMENT

In a typical reaction in accordance with this invention a solution of naphthalene in heptane and the carboxylic acid are contacted with the catalyst in an oxygen containing atmosphere at a reaction temperature in the range of from about 100° to 300° C. and preferably from about 140° to 200° C. and at from about 1 to 100, preferably 1 to 10 atmospheres and most preferably at or near atmospheric pressure. The molecular oxygen can be oxygen, per se, or any gaseous mixture containing molecular oxygen. For instance, molecular oxygen can be in the form of air for convenience. The catalyst can be a mixture of $(CH_3COO)_2Pd$ and $(CH_3COO)_3Sb$, for instance, in a molar ratio of about 1:1. This molar ratio of Pd:Sb can vary within the range of from 1:0.1 to 1:20 and is preferably within the range of from 1:0.1 to 1:10. The optional compound of chromium, cobalt, nickel, manganese, iron or tin can be present in the catalyst in a molar ratio of from 0 to 1 to 20 to 1 per mole of palladium and antimony in the catalyst. During the reaction usually the liquid reaction mixture slowly turns dark brown and the water formed is continuously removed conveniently by entrainment with the organic solvent for the naphthalene which is continuously removed by distillation as the reaction proceeds. The major product (and in most cases the only product) of the reaction, the naphthyl carboxylate, far exceeds the best yields reported in the prior art with essentially quantitative selectivity. As previously mentioned, the naphthyl carboxylate thus obtained can be hydrolyzed if so desired to produce naphthol or naphthols by known means and the carboxylic acid and catalyst can be recycled back into the oxidation reaction.

Because essentially no naphthol is produced in the oxidation process of this invention, it is believed that catalyst activity is maintained for long periods of time under continuous use. The rapid removal of water from the reaction mixture is probably at least partly responsible for the absence of naphthol in the reaction product. The presence of naphthol in the reaction product if it should occur is believed to be responsible for catalyst fouling and resulting short catalyst life. The process of this invention is further illustrated in the following Examples.

EXAMPLE I

The acetoxylation of naphthalene was carried out in a glass reactor, furnished with a thermometer, mechanical stirrer, Dean Stark type collector equipped with a reflux condenser and gas and liquid tubes. The reactor was charged with 43.3 g. (300 m mols) of octanoic acid, 10 g. (78 m mols) of naphthalene, 0.17 g. (0.75 m mols) of $Pd(OAc)_2$, 0.22 g. (0.75 m mols) of $Sb(OAc)_3$ and 0.17 g. (0.75 m mols) of $Cr(OAc)_3.H_2O$ (Pd/Sb/Cr=1:1:1). To this, 10 mols of heptane were added and the reaction mixture was stirred continuously the reaction temperature was maintained at about 170° C. and the oxygen was bubbled through the reaction liquid at a flow rate of about 50 cc. per minute. Water formed during the reaction and was removed continuously as it formed azeotropically with heptane. The reaction temperature was maintained within 2° C. plus or minus from 170° C. during the entire course of the reaction. The reaction was continued this way for 4 hours during which time about 1.3 mol. of water was produced. GLC analysis of the reaction mixture after the 4 hour reaction time showed that about 85% of the naphthalene was converted with almost quantitative selectivity (about 100%) to the naphthyl ester of octanoic acid (16.8 g.; 66 m mols). Only a small amount of $CO_2$ (less than 0.3 g.) was produced. Moles of naphthyl ester produced per mole of palladium catalyst per hour (defined as catalytic turn over numbers, T.N.) were found to be 16.5. The isomer distribution (alpha vs. beta) was observed to be 92% (alpha-naphthyl ester) vs. 8% (beta-naphthyl ester).

Other reactions carried out under identical reaction conditions and replacing heptane with other hydrocarbon solvents such as octane and nonane resulted in similar results.

EXAMPLE II

This reaction was carried out exactly as in the preceding example except that 46.9 g. (305 m mols) of octanoic acid, 10.1 g. (79 m mols) of naphthalene, 0.08 g. (0.35 m mols) of $Pd(OAc)_2$, 0.48 g. (1.6 m mols) of $Sb(OAc)_3$ and 0.09 g. (0.35 m mols) of $Cr(OAc)_3.H_2O$ and 10 ml. of heptane were charged. Analysis showed that 30% of the naphthalene charged was converted to produce 24 m moles of naphthyl ester of octanoic acid (5.4 g.) with almost 100% selectivity. The catalytic T.N. calculated to be about 69 per 5 hours. Only a trace amount of $CO_2$ was produced.

EXAMPLE III

This reaction was carried out with a slight variation to the procedure of example I. A solution of naphthalene was made in heptane (10% solution by wt.). This was introduced continuously into the reactor at a slow rate (0.5 ml./minute). The reactor was initially charged with 41 g. (284 m mols) of octanoic acid, 1.35 g. (6 m mols) of Pd(OAc)$_2$, 1.80 g. (6 m mols) of Sb(OAc)$_3$, 1.48 g. (6 m mols) of Cr(OAc)$_3$.H$_2$O and 5 ml. of the naphthalene solution in heptane. Reaction was carried out at 160±2° C. and O$_2$ was introduced at the rate of 50 cc/min. Naphthalene solution in heptane was pumped slowly (0.5 ml/minute) into the reaction mixture. Excess heptane and the water formed in the reaction was removed continuously which also helped in maintaining the reaction temperature at 160±2° C. The reaction was continued this way for 5 hours during which time, 14.3 g. (112 m mols) of naphthalene was introduced in the reactor. The GLC analysis of the reaction mixture revealed that in 5 hours. About 82% of the naphthalene introduced was converted to produce almost quantitatively (about 100% selectivity) the naphthyl ester (23 g.; 91 m mols).

EXAMPLE IV

In this experiment, a Soxhlet extraction type technique was utilized for introducing naphthalene into the reactor. The solid naphthalene was placed in a container and brought into the reactor by dissolving it with an inert solvent such as heptane.

In a typical experiment, 48 g. (333 m mols) of octanoic acid, 1.35 g. (6 m mols) of Pd(OAc)$_2$, 1.80 g. (6 m mols) of Sb(OAc)$_3$ and 1.48 g. (6 m mols) of Cr(OAc)$_3$.H$_2$O were charged to the reactor. Solid naphthalene (8.2 g.; 63 m mols) was placed in a container equipped with condenser and attached with the Dean-Stark tube. 8 ml. of heptane was used as an inert solvent in the reactor. The reaction mixture was stirred mechanically and the reaction was continued at 160°±2° C. for 5 hours during which time, all the naphthalene was dissolved and brought into the reactor by refluxing heptane. GLC analysis after 5 hours showed that all the naphthalene introduced to the reactor was converted (100% conversion) to give the naphthyl ester (15.6 g.; 62.0 m mols). Only a small amount of CO$_2$(0.3 g.) was produced.

EXAMPLE V

This reaction was carried out exactly as in Example I except that 48 g. (333 m mols) of octanoic acid, 3.2 g. (25 m mols) of naphthalene, 1.35 g. (6 m mols) of Pd(OAc)$_2$ and 1.8 g. (6 m mols) of Sb(OAc)$_3$ were used as reaction charge. No chromium salt was used in this experiment. The reaction was carried out at 160±2° C. for 5 hours. GLC analysis of the mixture revealed that 100% naphthalene was converted to naphthyl ester with about 100% selectivity. The isomer distribution was found to be about 80% alpha- and about 20% beta-naphthyl ester.

EXAMPLE VI

This reaction was carried out exactly as in example III except that 2.0 g. (0.16 m mols) of naphthalene was introduced and the catalyst used contained no chromium salts. After 5 hours of reaction, 100% of the naphthalene was converted to produced naphthyl ester.

EXAMPLE VII

This reaction was carried out exactly as in example V except that Mn(OAc)$_3$ (3 m mols) was also added in conjunction with 3 m mols of each Pd(OAc)$_3$ and Sb(OAc)$_3$. The naphthalene charged was 10 g. (78 m mols). In 3 hours of reaction at 170°±5° C., about 20% of the naphthalene was converted to produce naphthyl esters. Only a small amount of CO$_2$ (0.35 g.) was produced.

EXAMPLE VIII

This reaction was carried out in a similar way as in Example III except that glyme (the dimethyl ether of ethylene glycol) was used as the solvent instead of heptane and 14.5 g. of naphthalene was introduced in the reactor. Because of the water solubility of glyme, the water and glyme were removed continuously at a rate to allow the reaction temperature at 160±2° C. GLC analysis showed that about 10% of the naphthalene was converted to produce naphthyl ester. Almost exclusively the alpha-naphthyl ester (greater than 98%) was produced.

EXAMPLE IX

This procedure was carried out exactly as in the preceding example except that tetrahydrofuran was used as the solvent. After 5 hours of reaction at 160±2° C., GLC analysis showed that about 12% of the naphthalene was converted to naphthyl ester.

EXAMPLE X

This reaction was carried out exactly as in Example V except that 66 g. (338 m mols) of lauric acid was used instead of octanoic acid, and 10 g. (78 m mols) of naphthalene were charged. The reaction was carried out at 160±2° C. for 5 hours which resulted in about 30% naphthalene conversion to produce naphthyl ester of lauric acid (99% selectivity). The isomer distribution was found to be about 60% alpha- and about 40% beta-naphthyl ester.

EXAMPLE XI

This reaction was carried out as in Example I except that 66 g. (333 m mols) of lauric acid, 10 g. (78 m mols) of naphthalene, 1.35 g. (6 m mols) of Pd(OAc)$_2$, 1.8 g. (6 m mols) of Sb(OAc)$_3$ and 1.48 g. (6 m mols) of Cr(OAc)$_3$.H$_2$O were used as the reaction charge. 10 ml. of heptane was used as solvent. After 5 hours of reaction as 170±5° C. 100% naphthalene conversion was observed giving the naphthyl ester of lauric acid.

EXAMPLE XII

This experiment was carried out using biphenyl as the reactant in place of naphthalene. The reaction was carried out exactly as in the preceding example except that 10 g. (67 m mols) of biphenyl was used instead of naphthalene and 48 g. (333 m mols) of octanoic acid was used instead of lauric acid. The Pd/Sb/Cr catalyst was used in half the amounts of the preceding example, i.e., 0.67 g. (3 m mols) of Pd(OAc)$_2$, 0.9 g. (3 m mols) of Sb(OAc)$_3$ and 0.75 g. (6 m mols) of Cr(OAc)$_3$. The reaction was carried out at 170±2° C. for 5 hours and the water produced (2 ml.) was entrained with heptane. GLC analysis showed that about 65% of the biphenyl was converted to produce the biphenyl ester of octanoic acid. The isomer distribution found was about 62% ortho, about 30% meta and 8% para-phenyl ester.

EXAMPLE XIII

A. This experiment illustrates the differences between the reactions with and without using inert solvent. In this, the reactor was charged with the reactants exactly as described in Example V except that no heptane was used and 10 g. of naphthalene was charged. After 5 hours of reaction, GLC analysis showed that 31% of the naphthalene reacted to produce the naphthyl ester of octanoic acid (67% selectivity) and the undesirable by-product binaphthyl (33% selectivity).

B. Similarly in another experiment, when dodecanedioic acid (64 g., 278 m mols) was used instead of octanoic acid, only 12% conversion of naphthalene took place giving naphthyl ester (45% selectivity) and undesirable binaphthyls (55% selectivity).

C. In another experiment using octanoic acid (48 g.; 333 m mols), when chromium salt, 1.48 g. (6 m mols), of $Cr(OAc)_3H_2O$ was added in conjunction with Pd/Sb (6 m mols each), in 5 hours 58% of 10 g. naphthalene was converted to give 60% selectivity to naphthyl ester and 40% to binaphthyls.

These experiments clearly demonstrate that in the absence of solvent, not only the lower conversions were observed but also the selectivity to naphthyl ester was lost dramatically and by-products, i.e., binaphthyls were obtained.

We claim:

1. An oxidation process for the manufacture of higher aryl esters comprising contacting the reaction mixture of a higher aromatic hydrocarbon selected from the group consisting of naphthalene, anthracene, biphenyl, phenanthrene, and terphenyls, an organic solvent, a carboxylic acid and molecular oxygen in the liquid phase at a temperature in the range of from 100° to 300° C., with a catalyst composed of a palladium carboxylate, an antimony carboxylate and optionally a carboxylate of at least one metal selected from the group consisting of chromium and manganese.

2. The process of claim 1 wherein the carboxylic acid has the formula $R(COOH)_n$ wherein n is an integer of 1 or more and R is a hydrocarbon group having at least 5−n carbon atoms, wherein the higher aromatic hydrocarbon is added continuously to the reaction mixture, and the water formed in the process is entrained with the organic water-immiscible solvent and removed continuously from the reaction mixture as the ester is formed.

3. The process of claim 2 wherein the higher aromatic hydrocarbon is naphthalene.

4. The process of claim 3 wherein the catalyst is composed of palladium and antimony carboxylates.

5. The process of claim 1 wherein the organic solvent is a linear hydrocarbon having the formula $C_nH_{2n+2}$ wherein n is a number from 4 to 14.

6. The process of claim 1 wherein the organic solvent is a linear or cyclic aliphatic ether.

7. The process of claim 2 wherein the higher aromatic compound is biphenyl.

8. The process of claim 2 wherein the catalyst is composed of palladium, antimony and chromium acetates.

9. The process of claim 2 wherein the catalyst is composed of palladium, antimony and manganese acetates.

* * * * *